(12) United States Patent
Brazdeikis et al.

(10) Patent No.: US 8,212,554 B2
(45) Date of Patent: Jul. 3, 2012

(54) INTRALUMINAL MAGNETO SENSOR SYSTEM AND METHOD OF USE

(75) Inventors: Audrius Brazdeikis, Missouri City, TX (US); Jaroslaw Wosik, Houston, TX (US); Paul Cherukuri, Houston, TX (US); Morteza Naghavi, Houston, TX (US)

(73) Assignees: The University of Houston System, Houston, TX (US); Board of Regents, The University of Texas Systems, Austin, TX (US)

( * ) Notice: Subject to any disclaimer, the term of this patent is extended or adjusted under 35 U.S.C. 154(b) by 667 days.

(21) Appl. No.: 11/918,205

(22) PCT Filed: May 11, 2006

(86) PCT No.: PCT/US2006/018129
§ 371 (c)(1),
(2), (4) Date: May 26, 2009

(87) PCT Pub. No.: WO2006/122203
PCT Pub. Date: Nov. 16, 2006

(65) Prior Publication Data
US 2009/0322323 A1 Dec. 31, 2009

Related U.S. Application Data

(60) Provisional application No. 60/679,937, filed on May 11, 2005.

(51) Int. Cl.
*G01R 33/02* (2006.01)
(52) U.S. Cl. ........ 324/244; 324/149; 324/248; 324/318; 600/424; 600/423; 600/436; 600/409; 600/407; 600/9; 600/12; 600/13

(58) Field of Classification Search .................. 324/207, 324/244, 149, 318, 423, 248; 600/424, 409, 600/431, 509, 421, 423, 436, 407, 9, 12, 600/13
See application file for complete search history.

(56) References Cited

U.S. PATENT DOCUMENTS
3,449,662 A 6/1969 Wood
(Continued)

FOREIGN PATENT DOCUMENTS
DE 4218635 12/1993
(Continued)

OTHER PUBLICATIONS

Wosik J et al: "A novel planar design of 200 MHz superconducting array" Proceedings of the International Society for Magnetic Resonance in Medicine, 11TH Scientific Meeting and Exhibition, Toronto, Ontario, Canada, Jul. 10-16, 2003, Jul. 10, 2003, p. 2373, XP002348446.

(Continued)

*Primary Examiner* — Huy Q Phan
*Assistant Examiner* — Alesa Allgood
(74) *Attorney, Agent, or Firm* — Robert W Strozier (57) ABSTRACT

A system (100) including a catheter mounted magneto sensor (114), such as a superconducting quantum interference device (SQUID), and methods using the system are disclosed, where the system and method are designed to detect changes in a magnetic field in a body of interest, such as a patient, to detect changes in a magnetic field in a patient, to identify loci in a target body that accumulate magnetic particles or to identify vulnerable plague in a patient.

7 Claims, 11 Drawing Sheets

U.S. PATENT DOCUMENTS

| | | | |
|---|---|---|---|
| 4,324,255 A | | 4/1982 | Barach et al. |
| 4,535,381 A | | 8/1985 | Rayburn |
| 4,672,972 A | * | 6/1987 | Berke .................... 600/422 |
| 5,293,119 A | | 3/1994 | Podney |
| 5,384,109 A | | 1/1995 | Klaveness et al. |
| 5,414,356 A | | 5/1995 | Yoshimura et al. |
| 5,496,534 A | * | 3/1996 | Klaveness et al. ........... 424/9.32 |
| 5,565,778 A | | 10/1996 | Brey et al. |
| 5,585,723 A | | 12/1996 | Withers et al. |
| 5,699,801 A | | 12/1997 | Atalar et al. |
| 6,052,610 A | * | 4/2000 | Koch .................... 600/424 |
| 6,121,776 A | | 9/2000 | Marek |
| 6,144,872 A | * | 11/2000 | Graetz .................... 600/409 |
| 6,171,240 B1 | | 1/2001 | Young et al. |
| 6,177,797 B1 | | 1/2001 | Srinivasan |
| 6,219,572 B1 | | 4/2001 | Young |
| 6,252,403 B1 | | 6/2001 | Alsop |
| 6,377,048 B1 | * | 4/2002 | Golan et al. ............... 324/318 |
| 6,615,071 B1 | | 9/2003 | Casscells, III et al. |
| 6,633,161 B1 | | 10/2003 | Vaughan, Jr. |
| 6,727,700 B2 | | 4/2004 | Marek |
| 6,798,204 B2 | | 9/2004 | Seeber et al. |
| 6,842,003 B2 | | 1/2005 | Heid et al. |
| 6,925,322 B2 | * | 8/2005 | Helfer et al. ............... 600/423 |
| 6,950,063 B2 | * | 9/2005 | Nesteruk et al. ........... 342/423 |
| 7,268,664 B2 | | 9/2007 | Tanaka et al. |
| 2001/0031919 A1 | * | 10/2001 | Strommer et al. ........... 600/424 |
| 2002/0067167 A1 | | 6/2002 | Romo et al. |
| 2002/0165448 A1 | | 11/2002 | Ben-Haim et al. |
| 2003/0028101 A1 | | 2/2003 | Weisskoff et al. |
| 2003/0095923 A1 | | 5/2003 | Ohkawa |
| 2003/0120270 A1 | * | 6/2003 | Acker .................... 606/41 |
| 2003/0216632 A1 | * | 11/2003 | McClure et al. ........... 600/409 |
| 2004/0130323 A1 | | 7/2004 | Oohashi et al. |
| 2004/0138558 A1 | | 7/2004 | Dunki-Jacobs et al. |
| 2004/0199072 A1 | * | 10/2004 | Sprouse et al. ........... 600/424 |
| 2005/0059852 A1 | | 3/2005 | Rioux et al. |
| 2005/0203368 A1 | * | 9/2005 | Verin .................... 600/407 |
| 2005/0209587 A1 | * | 9/2005 | Joye et al. ............... 606/21 |
| 2005/0283067 A1 | * | 12/2005 | Sobe .................... 600/409 |
| 2006/0142630 A1 | * | 6/2006 | Meretei .................... 600/9 |
| 2007/0013377 A1 | | 1/2007 | Wosik et al. |
| 2008/0278166 A1 | | 11/2008 | Wosik et al. |
| 2009/0177074 A1 | | 7/2009 | Brazdeikis et al. |
| 2009/0201016 A1 | | 8/2009 | Hattersley et al. |
| 2009/0295385 A1 | * | 12/2009 | Brazdeikis et al. ........... 324/309 |

FOREIGN PATENT DOCUMENTS

| | | |
|---|---|---|
| EP | 0595227 | 1/1998 |
| EP | 0895092 | 2/1999 |
| EP | 1251361 | 10/2002 |
| FR | 2616911 | 12/1988 |
| FR | 2689638 | 8/1993 |
| GB | 2109112 | 5/1983 |
| JP | 01-151438 | 9/1989 |
| JP | 02-084933 | 6/1990 |
| WO | WO9324848 | 12/1993 |
| WO | WO9729684 | 8/1997 |
| WO | WO0070356 | 11/2000 |
| WO | WO03/097125 | 11/2003 |
| WO | WO2006067692 | 6/2006 |
| WO | WO2006/122278 | 11/2006 |

OTHER PUBLICATIONS

Chow MS et al: "A two-channel HTS thin-film phased array coil for low field MRI" Proceedings of the International Society for Magnetic Resonance in Medicine, 11TH Scientific Meeting and Exhibition, Toronto, Ontario, Canada, Jul. 10-16, 2003, Jul. 10, 2003, p. 2372, XP002348447.

Malagoli A et al: "Radiofrequency response of Ag-sheathed (Bi,Pb)2Sr2Ca2Cu3O10+x superconducting tapes" Physica C, North-Holland Publishing, Amsterdam, NL, vol. 378-381, Oct. 2002, pp. 1087-1090, XP004383056, ISSN: 0921-4534.

Bock N A et al: "Multiple-mouse MRI" Magnetic Resonance in Medicine, Academic Press, Duluth, MN, US, vol. 49, No. 1, Jan. 2003, pp. 158-167, XP002281379, ISSN: 0740-3194.

International Search Report for WO06122203.
International Search Report for WO06122202.
International Search Report for WO06122278.
International Search Report for WO05078468.

* cited by examiner

INTRALUMINAL MAGNETO SENSOR SYSTEM AND METHOD OF USE

RELATED APPLICATIONS

This application claims priority to PCT Patent Application Serial No. PCT/US06/18129, filed 11 May 2006 (May 11, 2006 or 11 May. 2006): WO06/122203; published 16 Nov. 2006 (Nov. 16, 2006 or 16 Jan. 2006), which claims priority to U.S. Provisional Patent Application Ser. No. 60/679,937, filed 11 May 2005 (May 11, 2005 or 11 May 2005).

BACKGROUND OF THE INVENTION

1. Field of the Invention

The present invention relates to a catheter mounted magneto sensor system and method for detecting a magnetic field distribution and/or changes in a magnetic field distribution in an animal's body of interest including human bodies, patients.

More particularly, the present invention relates to an apparatus, for detecting a magnetic field distribution and/or changes in a magnetic field in an animal including an human, where the apparatus includes a catheter and a magneto sensor mounted on a distal end of the catheter, where the magneto sensor can be a superconducting quantum interference device (SQUID). The present invention is also directed to methods of using the magneto sensor apparatus to detect changes in a magnetic field in a patient, to identify loci in a target body that accumulate magnetic particles or to identify infection, inflammation, in particular, vulnerable plaque in a patient.

2. Description of the Related Art

U.S. Pat. No. 5,735,279 to Klavenes, et al. discloses the use of a SQUID magnetometer to detect magnetic changes in vivo. U.S. Pat. No. 6,027,946 to Weiteschies, et al. discloses the use of a SQUID detector to measure the spacial distribution of relaxing magnetic markers in vivo. U.S. Pat. No. 5,594,849 to Kuc, et al. discloses the use of SQUID magnetometers for measuring magnetic field intensity. U.S. Pat. No. 6,123,902 to Koch, et al. discloses the use of a SQUID detector to detect small amounts of bound analytes in a solution. U.S. Pat. No. 6,048,515 to Kresse, et al. discloses the use of nanoparticles comprising an iron containing core and a targeting polymer coating to determine the biological behavior of the biomagnetic particles, including nanoparticles.

However, there is still a need in the art for magneto sensor system, instruments incorporating such systems and method using such systems for detecting magnetic field distribution and/or changes in a magnetic field in an animal body of interest, including a body of a human patient.

SUMMARY OF THE INVENTION

The present invention provides a magnetic detection system including a catheter having a magneto sensor mounted on its distal end. The sensor is adapted to measure magnetic fields and/or magnetic field distributions associated with locations in an area of interest in an animal, including an human, body. The area of interest is generally accessible via an artery or a vein or other duct or channel that can accommodate a catheter.

The present invention provides a magnetic detection system including a catheter having a magneto sensor and a ultrasonic transmitter mounted on its distal. The sensor is adapted to measure magnetic fields and/or magnetic field distribution associated with locations in an area of interest in an animal, including an human, body. The ultrasonic transmitter, which can be a dual beam ultrasonic transmitter, is adapted to introduce a mechanical vibration to locations with in the area of interest.

The present invention provides a magnetic detection system including a catheter having a magneto sensor, a ultrasonic transmitter and a coil mounted on its distal. The sensor is adapted to measure magnetic fields and/or magnetic field distribution associated with locations in an area of interest in an animal, including an human, body. The ultrasonic transmitter, which can be a dual beam ultrasonic transmitter, is adapted to introduce a mechanical vibration to the locations with in the area of interest. The coil is adapted to introduce a modulation to the locations with in the area of interest.

The present invention provides a magnetic detection system including a catheter having a magneto sensor, a ultrasonic transmitter, a coil mounted on its distal and a magnetically active agent introduction conduit having an orifice disposed at or near the distal end of the catheter. The sensor is adapted to measure magnetic fields and/or magnetic field distribution associated with locations in an area of interest in an animal, including an human, body. The ultrasonic transmitter, which can be a dual beam ultrasonic transmitter, is adapted to introduce a mechanical vibration to the locations with in the area of interest. The coil is adapted to introduce a modulation to the locations with in the area of interest. The conduit is designed to introduce a magnetically active agent into the area of interest.

The present invention also provides a method for measuring magnetic fields, magnetic field distributions and/or changes therein, where the method includes inserting a catheter of this invention into an artery, vein or other suitable structure in an animal, including an human and positioning a distal end of the catheter adjacent an area of interest of the animal. The method also includes the step of measuring a magnetic field distribution of the area of interest. The method may also include the step of making a series of magnetic field distribution measurements as the catheter is moved within the artery or vein to acquire a distribution along the artery or vein. The method also includes the step of administering a magnetically active agent to the animal before and/or after measuring the magnetic field distribution. The method may also include the step of making a second series of magnetic field distribution measurements as the catheter is moved within the artery or vein to acquire a distribution along the artery or vein after administration of the magnetically active agent. The method can also include applying a controlled external magnetic field to the area of interest to produce a controlled modulation of any magnetically active agent within loci within the area of interest, where the term external does not mean that the field is generated outside of the body necessarily as the external field in the catheter designed herein described can be produced at the distal end of the catheter using coils or other devices to generate controlled magnetic field at the distal end of the catheter. Of course, the external magnetic field can be generated outside of the body using any system for generating a controlled magnetic field. The method can also include applying an ultrasonic beam to the area of interest to induce mechanical vibrations of magnetically active agents accumulated in loci within the area of interest. The method may includes the step of comparing different distribution or field data to obtain data before and after administration, modulation or mechanical vibration. The method also includes analyzing the data to identify locations within the area of interest that evidence an accumulation of magnetically active agents. The analyzing step can also use imaging data such as ultrasonic data to register the magnetic data, where registration means that the magnetic data is made to conform to physical locations within the area of interest. The method can also include the step of measuring a physical and/or chemical property in, near or surrounding the area of interest. The method of the present invention may be employed for various medical diagnostic purposes, such as locating vulnerable plaque in a patient's body.

BRIEF DESCRIPTION OF THE DRAWINGS

The invention can be better understood with reference to the following detailed description together with the appended illustrative drawings in which like elements are numbered the same.

DETAILED DESCRIPTION OF THE INVENTION

The inventors have found that an apparatus and method based on the apparatus can be constructed that permits measuring magnetic fields, magnetic field distributions and/or changes in the fields or distributions utilizing a magnetic sensor disposed on a distal end of a catheter designed to be inserted into an artery, vein or other bodily structure suitable for the insertion of a catheter in an animal, including an human. The apparatus and methods are designed to be used in combination with the administration into the animal of a magnetically active agent, such as magnetically active nanoparticles. After introducing the agent into the animal, the agent will distribute throughout the animal according to uptake propensities of individual tissues or organs for the agent and according to a rate of expulsion of the agent from the tissue or organs. Certain tissues or structures in the body are less able to expel the agent and the agent tends to accumulate in these tissues or structures. Thus, by measuring a magnetic field distribution before, during and after administration, one can detect the uptake, accumulation and expulsion of the agent in an area of interest. The location or loci where the agent accumulates and persists represent structures or locations associated with ischemia, infarction, injury, inflammation, infection, tumor, bleeding, angiogenesis, abnormally high blood barrier permeability, abnormally high capillary permeability, clot formation, plaque, vulnerable plaque or other structures that accumulate the agent.

The present invention broadly relates to an apparatus including a catheter and a magneto sensor mounted on a distal end of the catheter, where the sensor is capable of measuring a magnetic field distribution of the area of interest or a magnetic field strength of a location within the area of interest. The catheter can be equipped with other elements such as a coil for exposing the area of interest or a location therein to a modulating magnetic field, an ultrasonic transmitter for inducing a mechanical vibration in the area of interest or location therein, and/or a magnetically active agent introduction assembly for introducing a magnetically active agent proximate the area of interest or a location therein.

The present invention broadly relates to a method for detecting changes in a magnetic field in an animal including a human including the step of inserting a distal end of an apparatus including a catheter and a magneto sensor mounted on a distal end of the catheter into an artery or vein of an animal including a human, until the distal end is positioned in or adjacent to an area of interest. Once the distal end of the catheter is in or adjacent to the area of interest (AOI), detecting a sensor response resulting from changes in a magnetic field at the AOI.

Suitable Materials and Sensors

Suitable magneto or magnetic sensors for use in this invention include, without limitation, magnetooptical sensors, flux gate magnetometers, Hall effect sensors, magnetic force sensors, magnetoresistive sensors, magnetoinductive sensors, magneto-resonance sensors, superconducting quantum interference device (SQUID) and/or mixtures or combinations thereof.

Suitable magnetically active agents for use in this invention include, without limitation, magnetic substances, such as molecules or particles, iron oxide or gadolinium containing materials, especially, nanomaterials—nanoparticles or the like, SPIO particles, ferromagnetic molecules or particles, ferrimagnetic molecules or particles, paramagnetic molecules, paramagnetic particles or mixtures or combinations thereof.

Catheters of this Invention

Referring now to FIGS. 1A-F, a plurality of embodiments of an intravascular magneto sensor apparatus of the present invention, generally 100, are shown. Looking at FIG. 1A, the apparatus 100 includes a catheter 102 having a distal end 104 and a sensor assembly 106 mounted at or on the distal end 104 the catheter 102. The sensor assembly 106 includes a sensor housing 108, a sensor cable 110, and a sensor head 112 comprising a magneto sensor 114. The magneto sensor may be a SQUID sensor, magneto-optical sensor, flux-gate magnetometer, Hall-effect sensor, magnetic-force sensor, magneto-resistive sensor, magneto-inductive sensor, magneto-resonance sensor or a combination thereof. The sensor cable 110 is attached to the sensor 114 at its distal end and extends through the catheter to an external power supply.

Figure 1A:
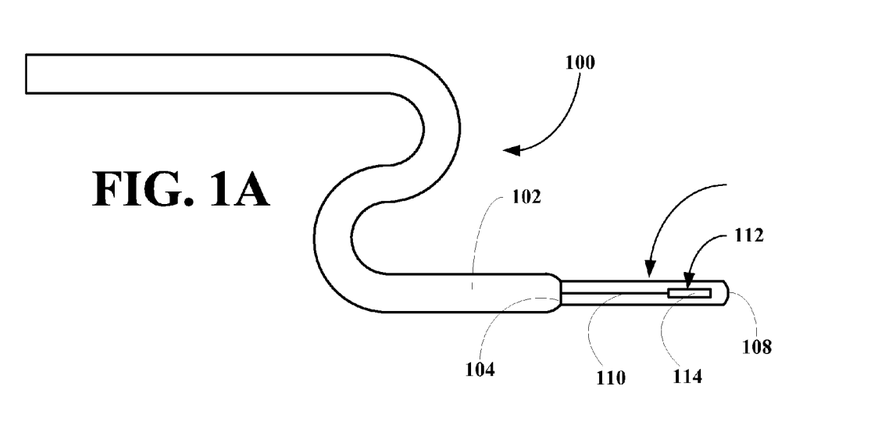
FIG. 1A depicts an embodiment of a catheter of this invention including a magneto sensor.
Figure 1B:
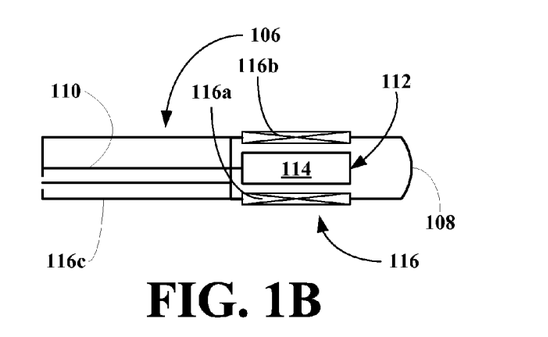
FIG. 1B depicts an embodiment of a catheter of this invention including a magneto sensor and a magnetizing element.

Looking at FIG. 1B, another sensor assembly 106 includes a sensor housing 108, a sensor cable 110, a sensor head 112 comprising a magneto sensor 114 and a magnetizing element 116 comprising a pair of coils 116a&b and a magnetizing element cable 116c. The magnetizing element cable 116c is attached to the coils 116a&b at its distal ends and extends through the catheter to an external power supply. Although the magnetizing element 116 is shown here as a pair of coils, the magnetizing element 116 can be any other element that can produce a controlled magnetic field, where the magnetic field can be any desired magnetic field including, without limitation, a static magnetic field, an amplitude varying magnetic field, a gradient magnetic field, a periodically varying magnetic field or any other type or combination of such field.

Figure 1C:
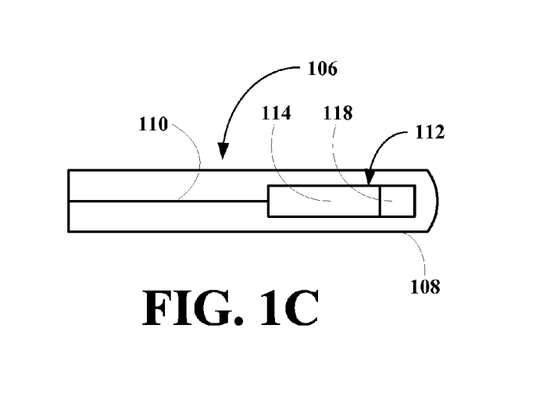
FIG. 1C depicts an embodiment of a catheter of this invention including a magneto sensor and auxiliary sensor type.

Looking at FIG. 1C, another sensor assembly 106 includes a sensor housing 108, a sensor cable 110, a sensor head 112 comprising a magneto sensor 114 and a secondary sensor 118 such as a temperature sensor, a pH sensor, a chemical sensor, an ion specific sensor, or a combination thereof.

Figure 1D:
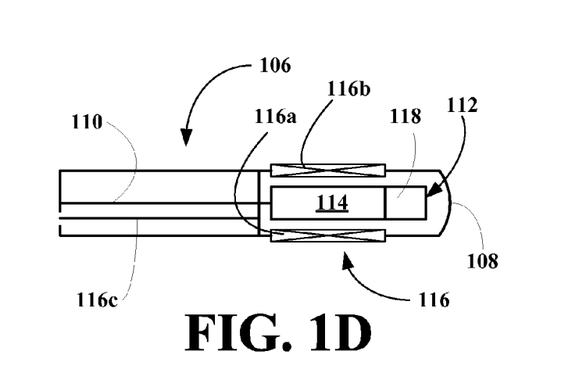
FIG. 1D depicts an embodiment of a catheter of this invention including a magneto sensor, a magnetizing element and auxiliary sensor type.

Looking at FIG. 1D, another sensor assembly 106 includes a sensor housing 108, a sensor cable 110, a sensor head 112 comprising a magneto sensor 114, a magnetizing element 116 comprising a pair of coils 116a&b and a magnetizing element cable 116c and a secondary sensor 118 such as a temperature sensor, a pH sensor, a chemical sensor, an ion specific sensor, or a combination thereof.

Figure 1E:
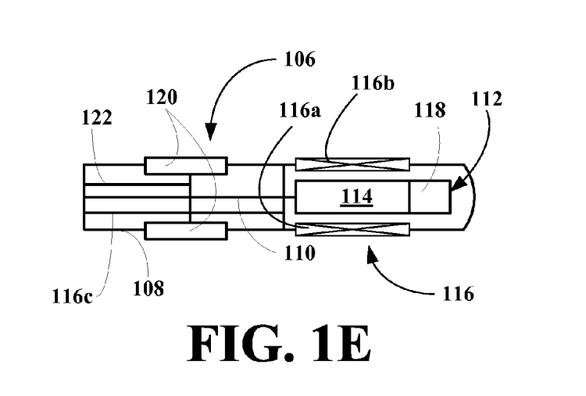
FIG. 1E depicts an embodiment of a catheter of this invention a magneto sensor, a magnetizing element, auxiliary sensor type and a ultrasonic transmitter.

Looking at FIG. 1E, another sensor assembly 106 includes a sensor housing 108, a sensor cable 110, a sensor head 112 comprising a magneto sensor 114, a magnetizing element 116 comprising a pair of coils 116a&b and a magnetizing element cable 116c, a secondary sensor 118, such as a temperature sensor, a pH sensor, a chemical sensor, an ion specific sensor, or a combination thereof, and an ultrasonic transmitter 120 and a transmitter cable 122, where the transmitter 120 is adapted to induce a mechanical vibration of a desired frequency in the area of interest or a location therein.

Figure 1F:
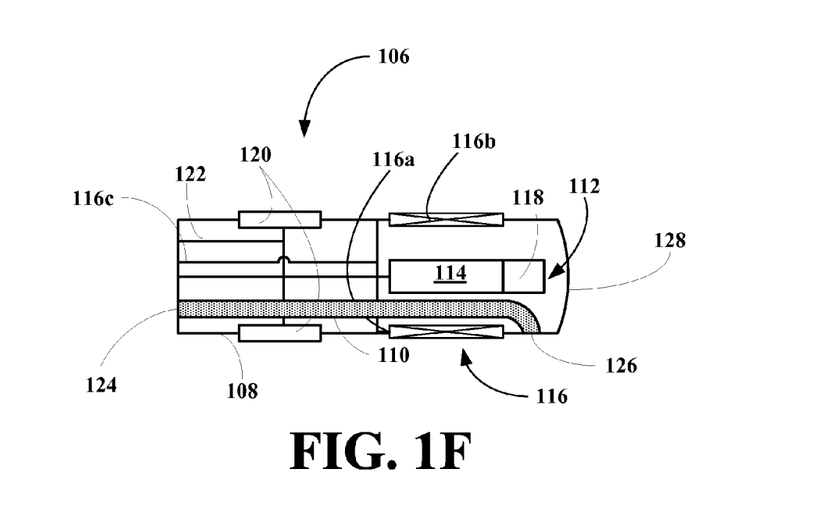
FIG. 1F depicts an embodiment of a catheter of this invention a magneto sensor, a magnetizing element, auxiliary sensor type, a ultrasonic transmitter and a magnetically active agent delivery system.

Looking at FIG. 1F, another sensor assembly 106 includes a sensor housing 108, a sensor cable 110, a sensor head 112 comprising a magneto sensor 114, a magnetizing element 116 comprising a pair of coils 116a&b and a magnetizing element cable 116c, a secondary sensor 118, such as a temperature sensor, a pH sensor, a chemical sensor, an ion specific sensor, or a combination thereof, and an ultrasonic transmitter 120 and a transmitter cable 122, where the transmitter 120 is adapted to induce a mechanical vibration of a desired frequency in the area of interest or a location therein. The assembly 106 also includes a magnetically active agent delivery conduit 124 ending in an orifice 126 positioned near a distal end 128 of the housing 108.

Referring now to FIGS. 2A-D, four embodiments of cryogenic sensor assemblies 206 are shown. Looking at FIG. 2A, the cryogenic sensor assembly 206 includes a sensor housing 208 made of or lined with a thermal insulating material 210, a cryogenic enclosure 212, a sensor cable 214, a sensor head 216 comprising a SQUID sensor 218. The enclosure 212 includes a cryogenic fluid 220. In one embodiment of this device, the fluid is a liquid and in another embodiment, the fluid is a gas.

Figures 2A, 2B:
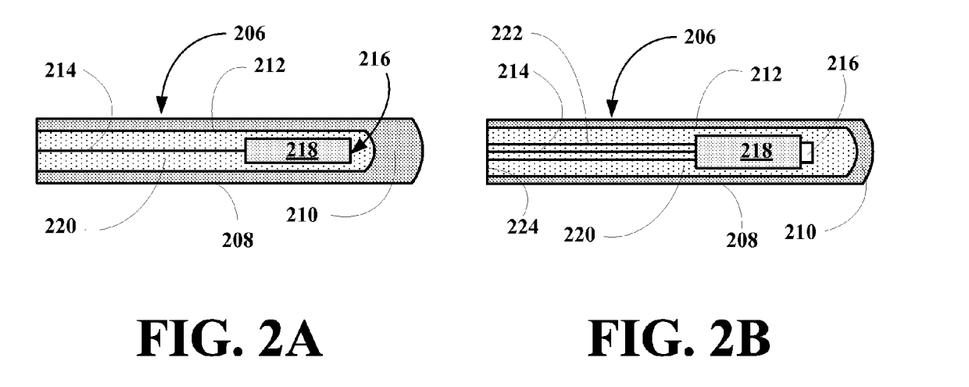
FIG. 2A depicts an embodiment of a cryogenic sensor assembly of this invention including a magneto sensor and a cryogenic enclosure.
FIG. 2B depicts another embodiment of a cryogenic sensor assembly of this invention including a magneto sensor, a cryogenic enclosure and conduits for circulating a cryogenic fluid in the enclosure.

Looking at FIG. 2B, the cryogenic sensor assembly 206 includes a sensor housing 208 made of or lined with a thermal insulating material 210, a cryogenic enclosure 212, a sensor cable 214, a sensor head 216 comprising a SQUID sensor 218. The enclosure 212 include a cryogenic fluid 220. The enclosure 212 includes a feed conduit 222 and a return conduit 224. The conduits extend from the enclosure 212 through the catheter and to a source of cryogenic fluid, where the conduits are designed to permit a cryogenic fluid to be circuited into the enclosure to maintain help maintain the SQUID below is superconducting transition temperature.

Figure 2C:
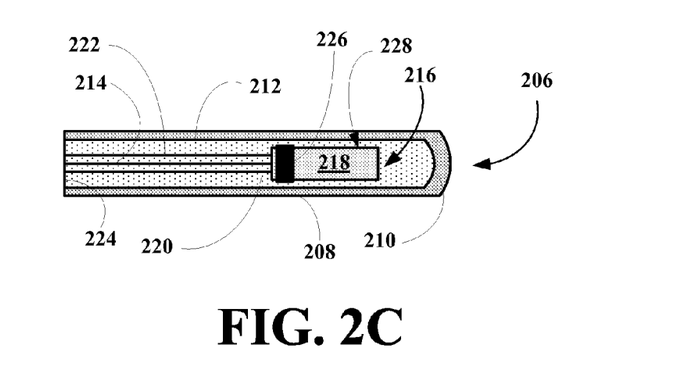
FIG. 2C depicts another embodiment of a cryogenic sensor assembly of this invention including a magneto sensor, a cryogenic enclosure, conduits for circulating a cryogenic fluid in the enclosure, and a thermally conducting handle.

Looking at FIG. 2C, the cryogenic sensor assembly 206 includes a sensor housing 208 made of or lined with a thermal insulating material 210, a cryogenic enclosure 212, a sensor cable 214, a sensor head 216 comprising a SQUID sensor 218. The enclosure 212 includes a cryogenic fluid 220. The enclosure 212 includes a feed conduit 222 and a return conduit 224. The assembly 206 also includes a heat conducting handle 226 in thermal conducting contact with the sensor 218 and extending outward from the sensor 218, away from a terminal region 228 of the sensor 218. The conduits extend from the enclosure 212 through the catheter and to a source of cryogenic fluid, where the conduits are designed to permit a cryogenic fluid to be circuited into the enclosure to maintain help maintain the SQUID below is superconducting transition temperature.

Figure 2D:
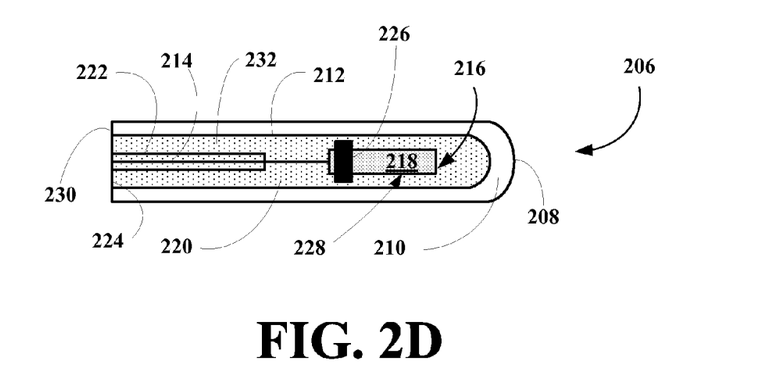
FIG. 2D depicts another embodiment of a cryogenic sensor assembly of this invention including a magneto sensor, a cryogenic enclosure, conduits for circulating a cryogenic fluid in the enclosure, a thermally conducting handle, and a vacuum enclosure; fluid in the enclosure, a thermally conducting handle, and a vacuum enclosure.

Looking at FIG. 2D, the cryogenic sensor assembly 206 includes a sensor housing 208 supporting a vacuum 210 adapted to act as an insulating layer, a cryogenic enclosure 212, a sensor cable 214, a sensor head 216 comprising a SQUID sensor 218. The enclosure 212 include a cryogenic fluid 220. The enclosure 212 includes a feed conduit 222 and a return conduit 224. The assembly 206 also includes a heat conducting handle 226 in thermal conducting contact with the sensor 218 and extending outward from the sensor 218, away from a terminal region 228 of the sensor 218. The assembly 206 may also includes a vacuum conduit 230 connected to the vacuum enclosure 230 and extending through the catheter to a vacuum device. The conduits extend from the enclosure 212 through the catheter and to a source of cryogenic fluid, where the conduits are designed to permit a cryogenic fluid to be circuited into the enclosure to maintain help maintain the SQUID below is superconducting transition temperature.

Figure 3:
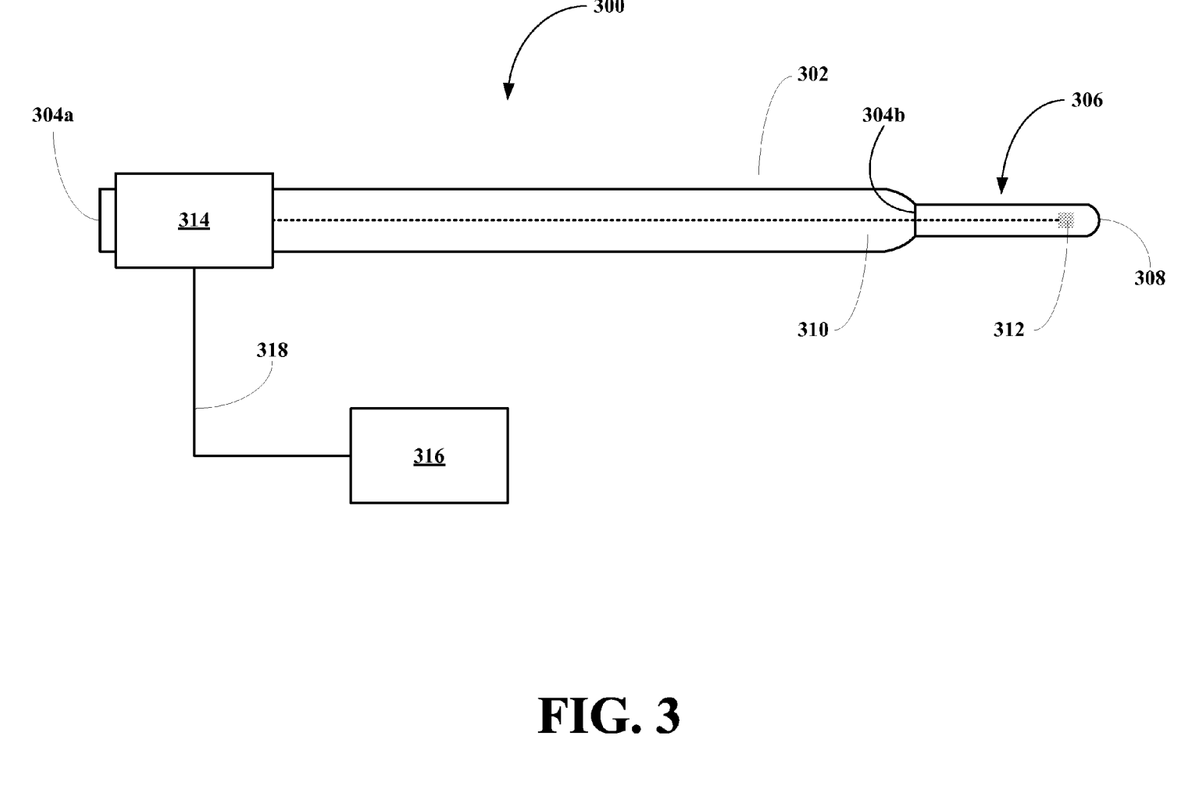
FIG. 3 depicts another catheter embodiment of the present invention.

Referring now to FIG. 3, another embodiment of a cryogenic intravascular magneto sensor apparatus of the present invention, generally 300, is shown to include a catheter 302 having a proximal end 304a and a distal end 304b and a sensor assembly 306 mounted at or on the distal end 304b the catheter 302. The sensor assembly 306 includes a sensor housing 308, a sensor cable 310, and a sensing element 312. The sensing element can be a SQUID sensor, magneto optical sensor, flux-gate, hall-effect sensor, cantilever-based sensor, magnetoresistive sensor, magnetoinductive sensor, magneto-resonance sensor or a combination thereof. The apparatus 300 also includes a receiver 314 in electrical communication with the sensing element 312 via the cable 310. In this embodiment, the sensing element 312 is operatively connected to the receiver 314. The receiver 314 is operatively connect to a detector 316 via a receiver cable 318. In one embodiment of this type of catheter, the receiver 314 is a pickup coil. In another embodiment of this type of catheter, the receiver is a gradiometer.

Method for Using the Systems of this Invention

Figure 4:
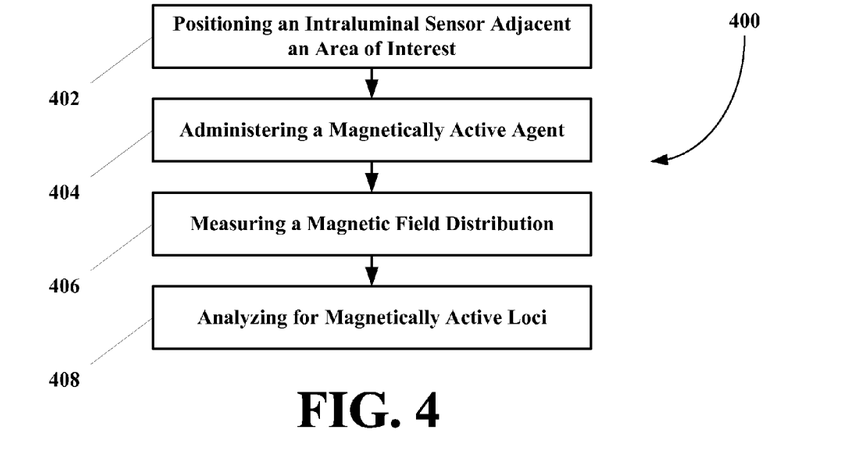
FIG. 4 depicts a flowchart of an embodiment of a method of the present invention.

Referring now to FIG. 4, an embodiment of a method of this invention for identifying magnetically active loci in a body of an animal including a human, generally 400, is shown to include a positioning step 402, where a catheter including an intraluminal magneto sensor of this invention is positioned within an artery, vein or other bodily structure amenable to catheter deployment, adjacent an area of interest in an animal, including an human. The method also includes an administering step 404, where a magnetically active agent is administered to the animal. After administration, the method also includes a measuring step 406, where a magnetic field distribution of an area of interest of the animal is measured using a magneto sensor. When a magnetically active agent, such as magnetic or magnetizable nanoparticles are administered into an animal be any known administration protocol, the agent distributes itself throughout the animal over time. Fortunately, the distribution is not uniform, as no diagnostic information could be retrieved from the magnetic field distribution if the distribution was uniform. Because different tissues, structures or locations within the entire animal, and especially with in the area of interest, accumulate the agent differently, the distribution is capable of identifying location or loci having high accumulations of the agent. These loci are believed to be associated with tissue structures that are not capable of readily eliminating the agent. Such loci include locations associated with ischemia, infarction, injury, inflammation, infection, tumor, bleeding, angiogenesis, abnormally high blood barrier permeability, abnormally high capillary permeability, clot formation, plaque, vulnerable plaque or other structures that accumulate the agent. After measuring the magnetic field, the method includes an analyzing step 408, where the distribution is analyzed to determine loci or locations within the area of interest that have relatively high accumulations of the agent relative to other locations in the area of interest.

Figure 5:
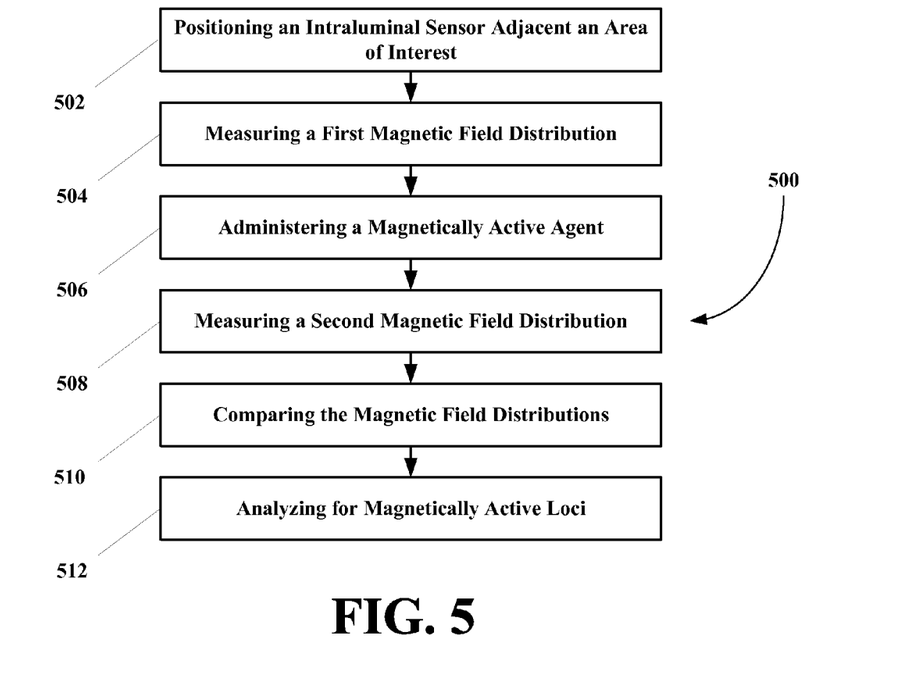
FIG. 5 depicts another flowchart of an embodiment of a method of the present invention.

Referring now to FIG. 5, another embodiment of a method of this invention for identifying magnetically active loci in a body of an animal including a human, generally 500, is shown to include a positioning step 502, where a catheter including an intraluminal magneto sensor of this invention is positioned within an artery, vein or other bodily structure amenable to catheter deployment, adjacent an area of interest in an animal, including an human. The method also includes a first measuring step 504, where a first magnetic field distribution of an area or region of interest in the animal is measured using a magneto sensor located external to the animal. After the first magnetic field distribution is measured, the method includes an administering step 506, where a magnetically active agent is administered to the animal. After administration, the method also includes a second measuring step 508, where a second magnetic field distribution of an area of interest of the animal is measured using the magneto sensor located external to the animal. Next, the method includes a comparing step 510, where the first and second distributions are compared. The method also includes an analyzing step 512, where the distributions and comparison are analyzed to determine loci within the area of interest having an accumulation of the magnetically active agent above a threshold accumulation amount. The threshold can be determined relative to a reference scale or can be determined from a scale produced from the distribution itself or from a combination of a reference scale and corrections factors taken from the distribution itself.

The comparison of a first and second magnetic field distributions includes information about the distribution of the magnetically active agent within the area of interest. The comparison can be a subtraction of the data after spacial registry so that the distribution relate to the same features in the area of interest. To aid in spacial registry, elements of known magnetic field behavior can be positioned on the body to assist in data analysis and data registry, especially in during the reverse transforms, where known spacial elements can be used to adjust the boundary conditions.

Figure 6A:
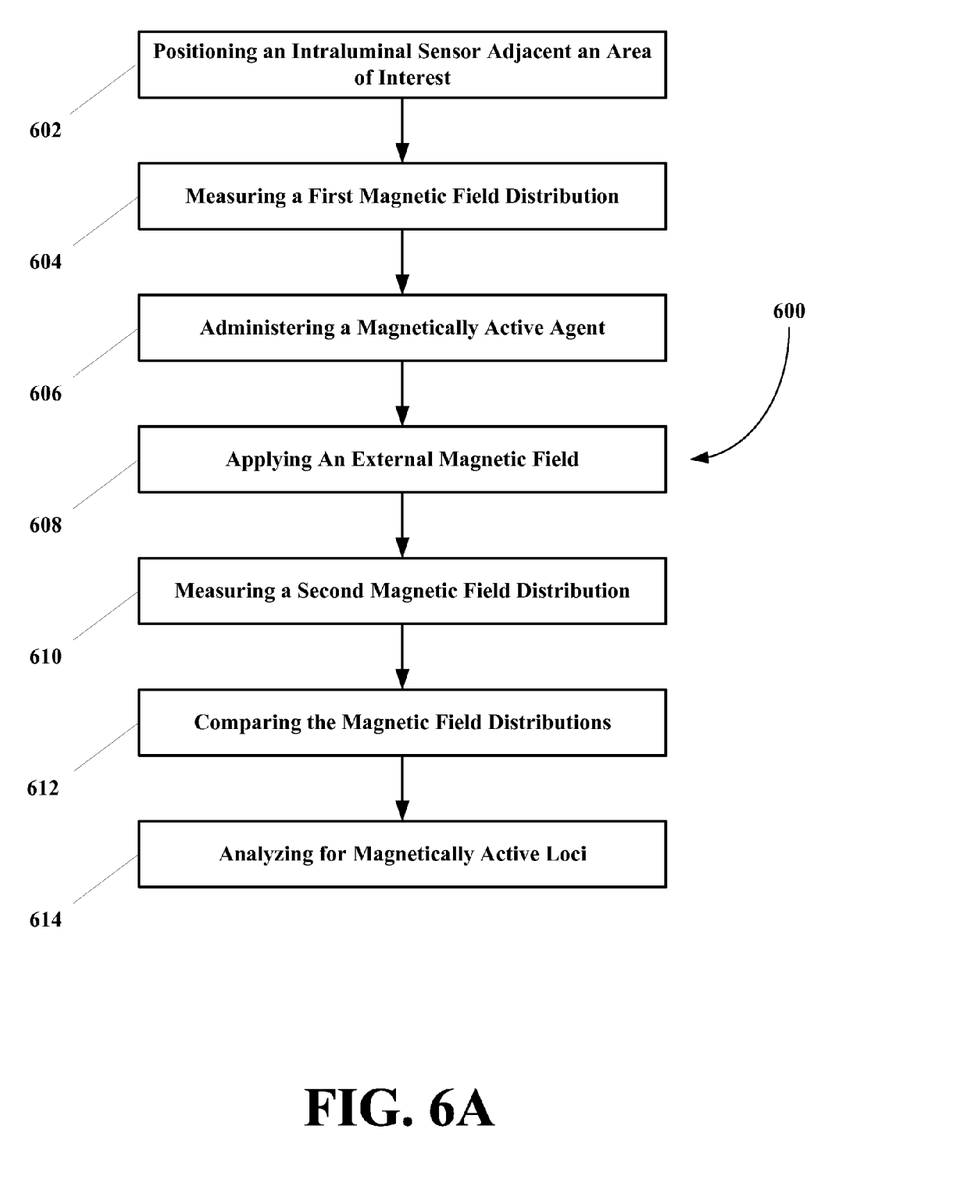
FIG. 6A depicts another flowchart of an embodiment of a method of the present invention.

Referring now to FIG. 6A, another embodiment of a method of this invention for identifying magnetically active loci in a body of an animal including a human, generally 600, is shown to include a positioning step 602, where a catheter including an intraluminal magneto sensor of this invention is positioned within an artery, vein or other bodily structure amenable to catheter deployment, adjacent an area of interest in an animal, including an human. The method also includes a first measuring step 604, where a first magnetic field distribution of an area or region of interest in the animal is measured using a magneto sensor located external to the animal. After the first magnetic field distribution is measured, the method includes an administering step 606, where a magnetically active agent is administered to the animal. After administration, the method also includes an applying an external magnetic field step 608, where the area of interest is exposed to an external magnetic field. While the area of interest is being exposed to the external magnetic field, the method includes a second measuring step 610, where a second magnetic field distribution of an area of interest of the animal is measured using the magneto sensor located external to the animal. Next, the method includes a comparing step 612, where the first and second distributions are compared. The method also includes an analyzing step 614, where the distributions and comparison are analyzed to determine loci within the area of interest having an accumulation of the magnetically active agent above a threshold accumulation amount. The threshold can be determined relative to a reference scale or can be determined from a scale produced from the distribution itself or from a combination of a reference scale and corrections factors taken from the distribution itself.

Figure 6B:
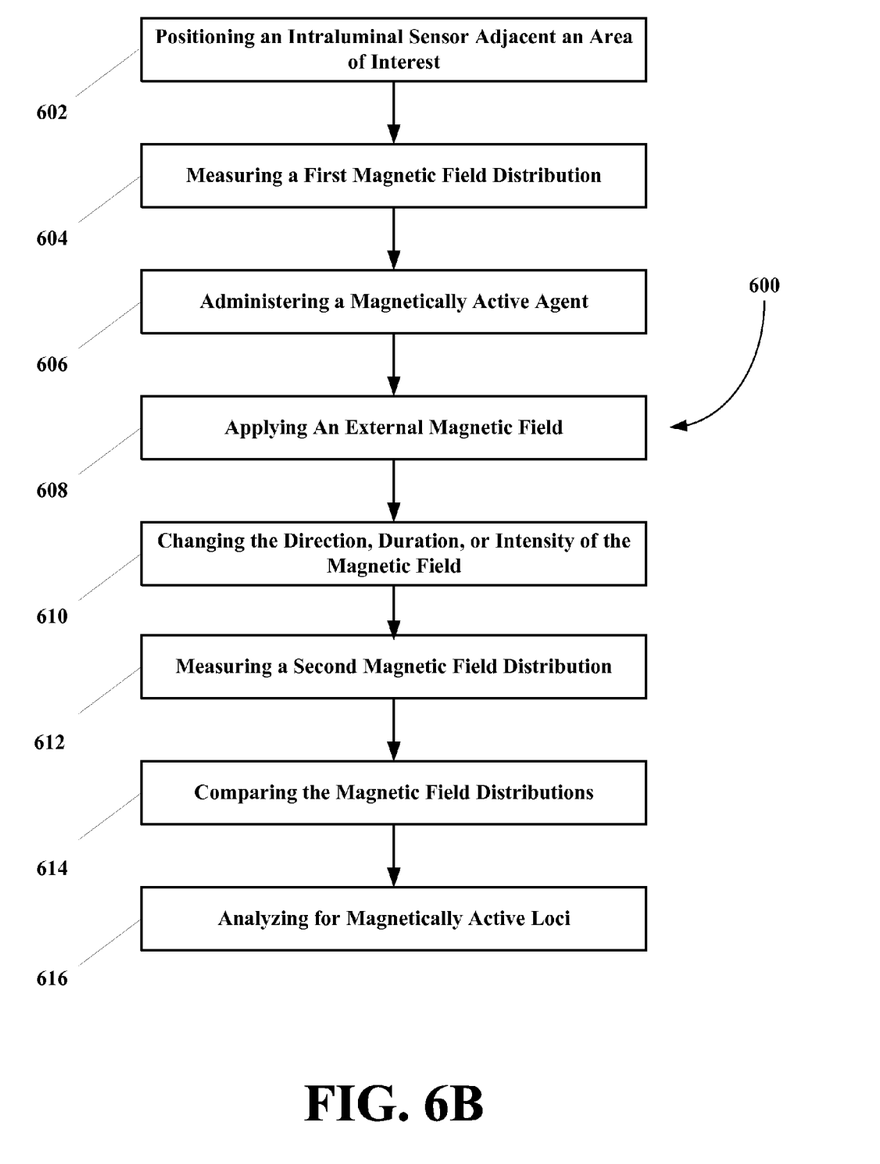
FIG. 6B depicts another flowchart of an embodiment of a method of the present invention.

Referring now to FIG. 6B, another embodiment of a method of this invention for identifying magnetically active loci in a body of an animal including a human, generally 600, is shown to include a positioning step 602, where a catheter including an intraluminal magneto sensor of this invention is positioned within an artery, vein or other bodily structure amenable to catheter deployment, adjacent an area of interest in an animal, including an human. The method also includes a first measuring step 604, where a first magnetic field distribution of an area or region of interest in the animal is measured using a magneto sensor located external to the animal. After the first magnetic field distribution is measured, the method includes an administering step 606, where a magnetically active agent is administered to the animal. After administration, the method also includes an applying an external magnetic field step 608, where the area of interest is exposed to an external magnetic field. The method also includes a changing a property of the applied magnetic field step 610, where one or more properties of the applied external magnetic field are changed in a controlled manner to enhance detection of the magnetically active agent in the area of interest, especially loci evidencing an accumulation of the agent. The properties of the field that can be changed include direction, duration, frequency and/or intensity. While the area of interest is being exposed to the external magnetic field and the property changes, the method includes a second measuring step 612, where a second magnetic field distribution of an area of interest of the animal is measured using the magneto sensor located external to the animal. Next, the method includes a comparing step 614, where the first and second distributions are compared. The method also includes an analyzing step 616, where the distributions and comparison are analyzed to determine loci within the area of interest having an accumulation of the magnetically active agent above a threshold accumulation amount. The threshold can be determined relative to a reference scale or can be determined from a scale produced from the distribution itself or from a combination of a reference scale and corrections factors taken from the distribution itself.

Figure 6C:
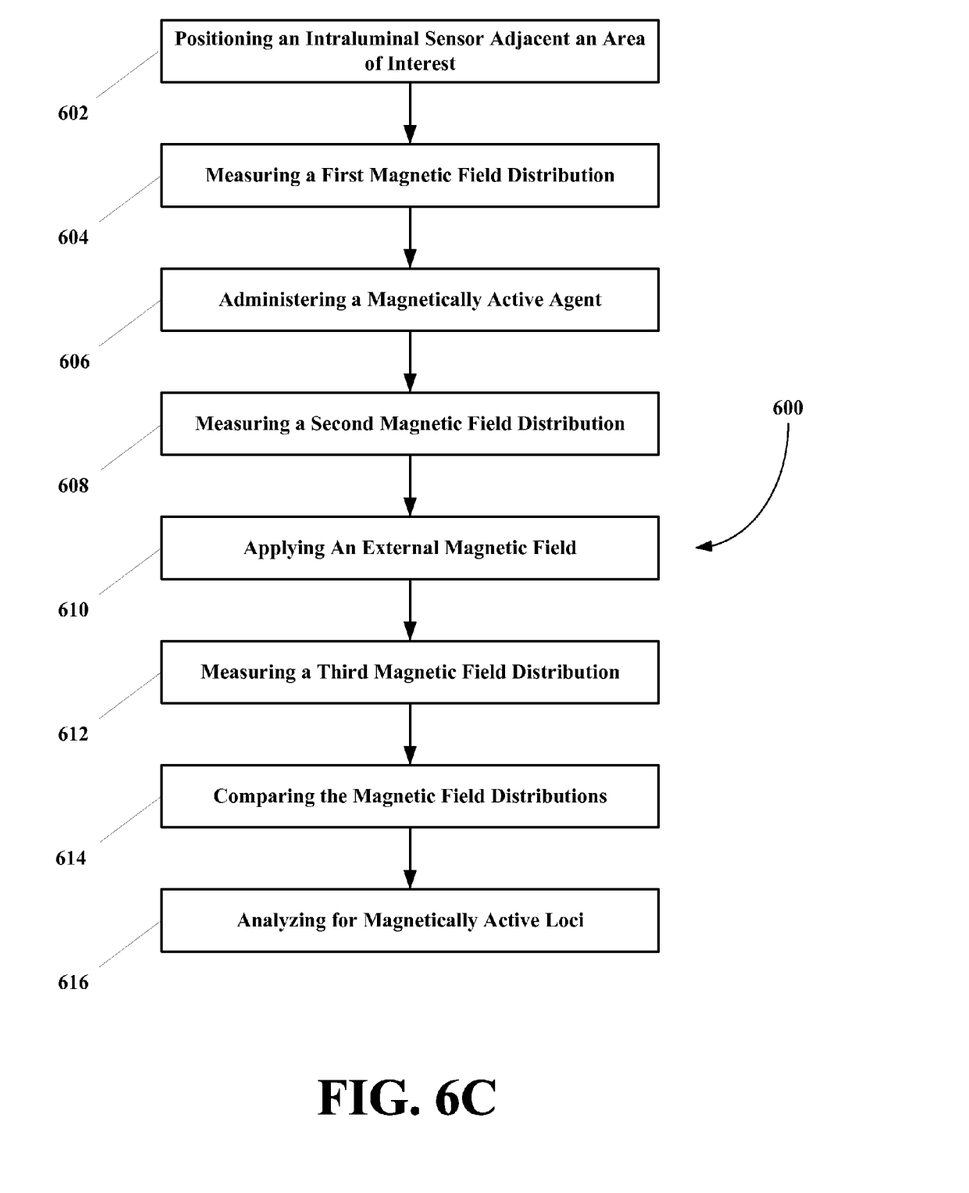
FIG. 6C depicts another flowchart of an embodiment of a method of the present invention.

Referring now to FIG. 6C, another embodiment of a method of this invention for identifying magnetically active loci in a body of an animal including a human, generally 600, is shown to include a positioning step 602, where a catheter including an intraluminal magneto sensor of this invention is positioned within an artery, vein or other bodily structure amenable to catheter deployment, adjacent an area of interest in an animal, including an human. The method also includes a first measuring step 604, where a first magnetic field distribution of an area or region of interest in the animal is measured using a magneto sensor located external to the animal. After the first magnetic field distribution is measured, the method includes an administering step 606, where a magnetically active agent is administered to the animal. After administration, the method also includes a second measuring step 608, where a second magnetic field distribution of an area of interest of the animal is measured using the magneto sensor located external to the animal. Next, the method includes an applying an external magnetic field step 610, where the area of interest is exposed to an external magnetic field. While the area of interest is being exposed to the external magnetic field, the method includes a third measuring step 612, where a third magnetic field distribution of an area of interest of the animal is measured using the magneto sensor located external to the animal. Next, the method includes a comparing step 614, where the first, second and third distributions are compared. The method also includes an analyzing step 616, where the distributions and comparison are analyzed to determine loci within the area of interest having an accumulation of the magnetically active agent above a threshold accumulation amount. The threshold can be determined relative to a reference scale or can be determined from a scale produced from the distribution itself or from a combination of a reference scale and corrections factors taken from the distribution itself.

Figure 6D:
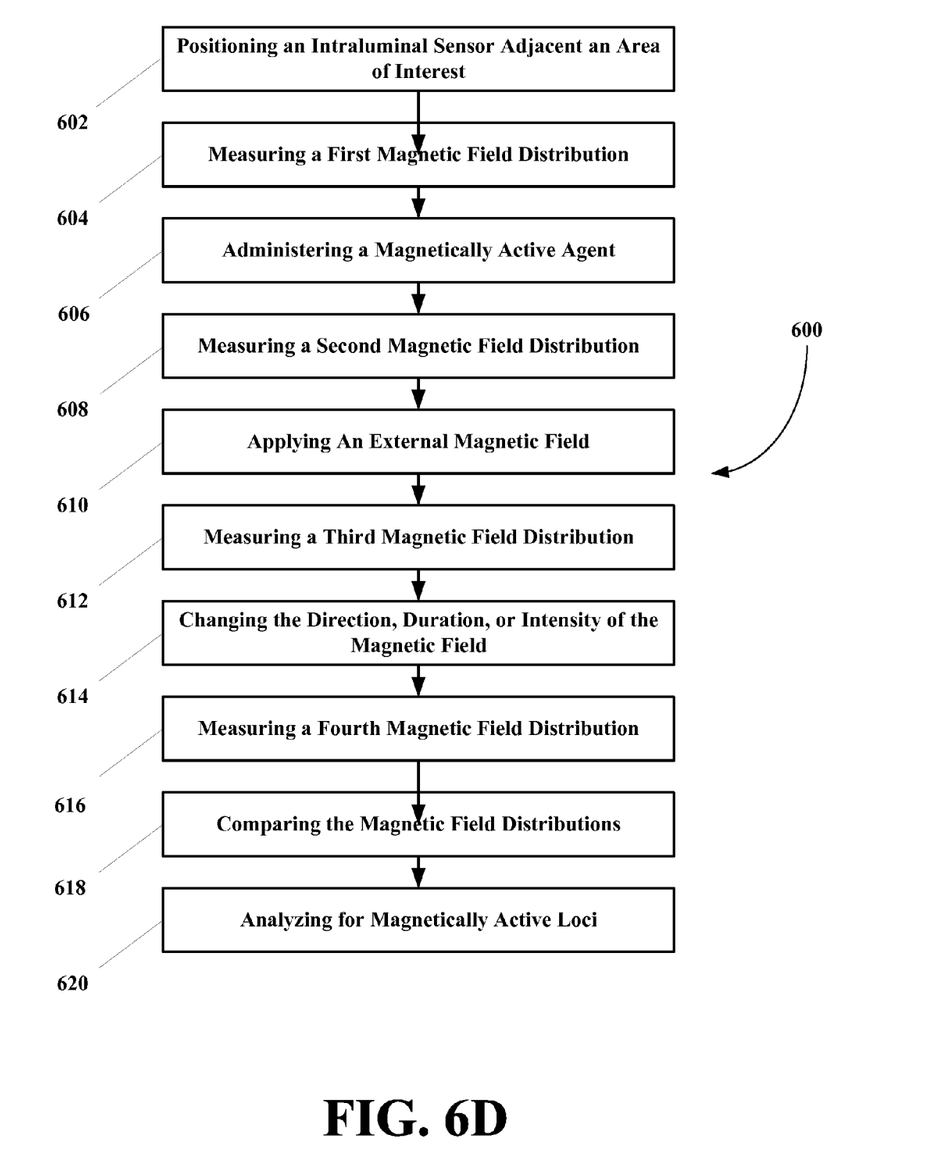
FIG. 6D depicts another flowchart of an embodiment of a method of the present invention.

Referring now to FIG. 6D, another embodiment of a method of this invention for identifying magnetically active loci in a body of an animal including a human, generally 600, is shown to include a positioning step 602, where a catheter including an intraluminal magneto sensor of this invention is positioned within an artery, vein or other bodily structure amenable to catheter deployment, adjacent an area of interest in an animal, including an human. The method also includes a first measuring step 604, where a first magnetic field distribution of an area or region of interest in the animal is measured using a magneto sensor located external to the animal. After the first magnetic field distribution is measured, the method includes an administering step 606, where a magnetically active agent is administered to the animal. After administration, the method also includes a second measuring step 608, where a second magnetic field distribution of an area of interest of the animal is measured using the magneto sensor located external to the animal. Next, the method includes an applying an external magnetic field step 610, where the area of interest is exposed to an external magnetic field. While the area of interest is being exposed to the external magnetic field, the method includes a third measuring step 612, where a third magnetic field distribution of an area of interest of the animal is measured using the magneto sensor located external to the animal. The method also includes a changing a property of the applied magnetic field step 614, where one or more properties of the applied external magnetic field are changed in a controlled manner to enhance detection of the magnetically active agent in the area of interest, especially loci evidencing an accumulation of the agent. The properties of the field that can be changed include direction, duration, frequency and/or intensity. While the area of interest is being exposed to the external magnetic field, the method includes a fourth measuring step 616, where a fourth magnetic field distribution of an area of interest of the animal is measured using the magneto sensor located external to the animal. Next, the method includes a comparing step 618, where the first, second, third and fourth distributions are compared. The method also includes an analyzing step 620, where the distributions and comparison are analyzed to determine loci within the area of interest having an accumulation of the magnetically active agent above a threshold accumulation amount. The threshold can be determined relative to a reference scale or can be determined from a scale produced from the distribution itself or from a combination of a reference scale and corrections factors taken from the distribution itself.

Figure 7A:
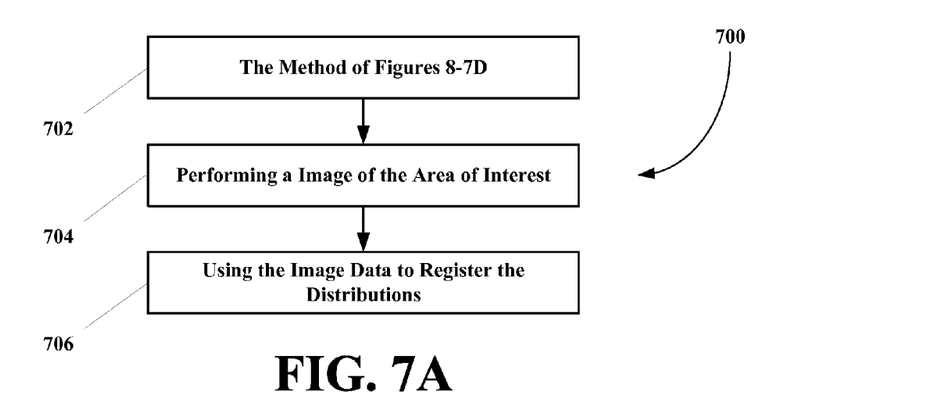
FIG. 7A depicts another flowchart of an embodiment of a method of the present invention.

Referring now to FIG. 7A, another embodiment of methods of this invention for identifying magnetically active loci in a body of an animal including a human, generally 700, are shown to include any of the previous method 702, with the addition of a imaging step 704 and a registering step 706. The imaging step 704 is adapted to couple the magnetic fluid distribution data with data from an imaging method such as magnetic resonance imaging (MRI), CAT scan imaging, computed tomography imaging, standard X-Ray imaging, ultrasonic or ultrasound imaging, or any other imaging method for obtaining a spatially relevant image. The registering step 706 is adapted to use the spatially relevant image data to associate the loci identified in the magnetic field distributions with their associated structures in the spatial image.

Figure 7B:
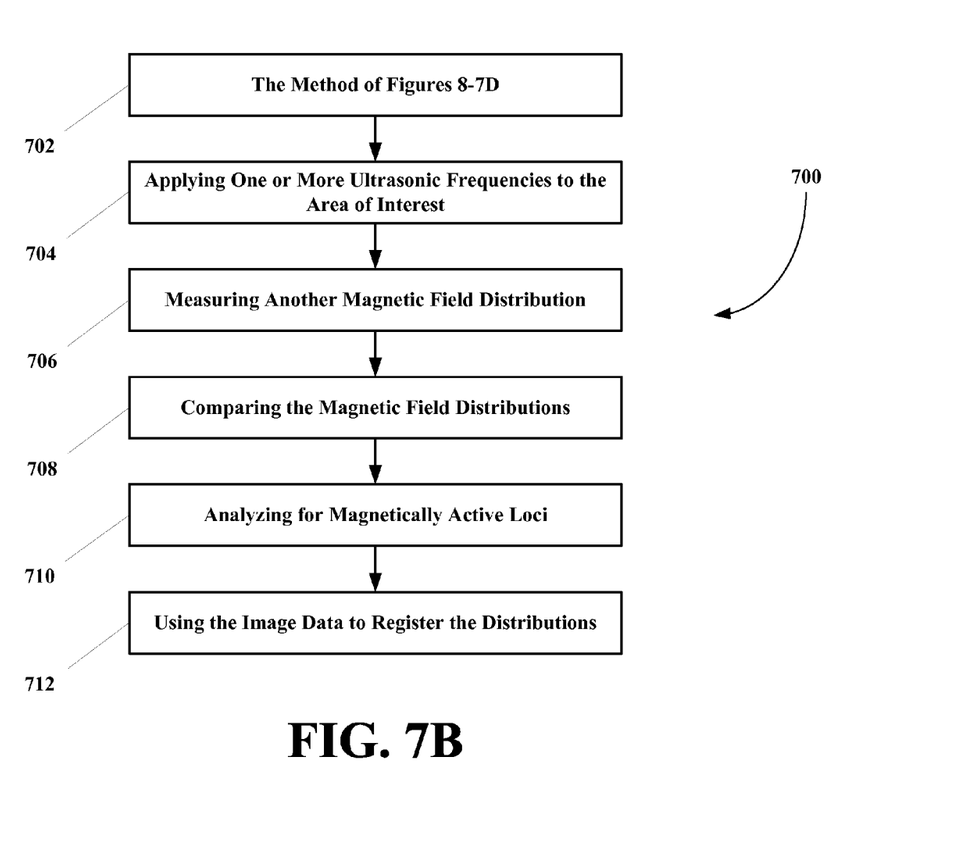
FIG. 7B depicts another flowchart of an embodiment of a method of the present invention.

Referring now to FIG. 7B, another embodiment of methods of this invention for identifying magnetically active loci in a body of an animal including a human, generally 700, are shown to include any of the previous method 702, with the addition of an ultrasonic irradiating step 704, an additional measuring step 706, an additional comparing step 708, an additional analyzing step 710 and a registering step 712. This method includes exciting the area of interest where the magnetic field distribution is being measured using ultrasound energy, while the distribution is being measured. The ultrasonic energy can be a single frequency and imparts a mechanical displacement to the magnetically active agents so that they can be more easily discerned from the magnetic fields generated by structures in the area of interest that generate their own magnetic field that tend to vary with time. The ultrasound energy can include two or more frequencies, where the frequencies are designed to interfere producing a mechanical vibration at a beat frequency resulting from their interference. By carefully selecting the beat frequency, the mechanical vibration frequency can be adjusted from the megahertz range, which is the range generated by ultrasound devices, into a frequency range between 1 Hz and 100,000 Hz.

The foregoing disclosure and description of the invention are illustrative and explanatory. Various changes in the size, shape, and materials, as well as in the details of the illustrative construction may be made without departing from the spirit of the invention.

This disclosure also discloses method and apparatus for detection, preferably with a superconducting quantum interference device magnetometer, of weak magnetic field variations originating from accumulated magnetic nanoparticles in electrically active tissues or body organs such as the heart. A difficulty in detecting accumulations magnetically active agents, such as magnetic nanoparticles, in such tissues is the presence of much stronger background magnetic fields in the tissues or generated in the tissues, e.g., the magnetic fields associated with cyclic bioelectrical activity of the heart. These generated or inherent magnetic field tend to mask, overshadow or obscure simultaneous detection of small local magnetic field perturbations to an applied magnetic field due to the accumulated magnetically active agents in these tissues. The another method of this invention includes the steps of using a pre-detection polarization of magnetic nanoparticles followed by discriminating detection of induced magnetic field perturbations within total measured flux. The pre-detection polarization sequence includes of time-varying excitation signal that is repeatedly triggered in a synchronized manner with a selected interval of a cardiac cycle and transmitted to whole body or local area of interest through a set of magnetic excitation coils or an acoustic beam transmitter. The detection is performed in a narrow frequency band, typically near a fundamental excitation frequency during the selected interval of the cardiac cycle. The magnetic elements on the catheter can also include a flux concentrator unit such as an ferromagnetic, metamaterial-based flux concentrator, and superconducting flux concentrator. These devices permit the magnetic field to be directed and concentrated relative to the sensor.

One embodiment of this method for measuring weak magnetic field perturbations due to locally accumulated magnetically active agents such as magnetically active nanoparticles at a target location, includes the steps of:

i. placing a magnetometer in the proximity of a area of interest of an animal, including a human;
ii. monitoring cardiac activity electrically or magnetically of the animal;
iii. determining a beginning of a trigger signal interval, $t_o$ by analyzing a cardiac cycle waveform of the animal;
iv. determining a duration, $t_d$ of the trigger signal interval;
v. generating a trigger signal waveform using parameters determined in steps (iii) and (iv);
vi. transmitting the trigger signal waveform to an arbitrary-form signal generator in order to generate an excitation signal waveform of chosen duration at the end of trigger;
vii. transmitting the excitation signal waveform through an excitation coil setup in order to achieve a required polarization of magnetic moments of nanoparticles;
viii. repeating steps (ii) through (vii);
ix. detecting a biomagnetic signal at the magnetometer;
x. extracting data from the selected interval of the cardiac cycle that equals a length of the excitation signal waveform;
xi. transforming the data from step (x) into a data form which indicates presence of nanoparticles at the target location.

Figure 8:
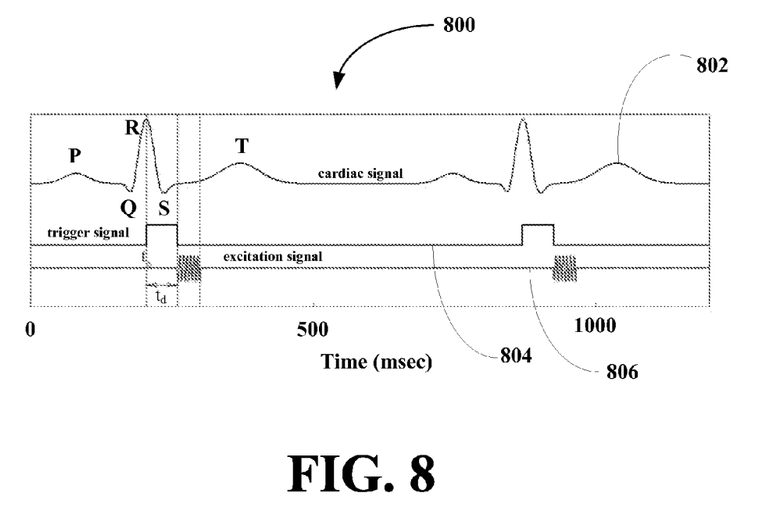
FIG. 8 is a block diagram of another embodiment of a method embodiment of the present invention.

Referring now to FIG. 8, the above method is illustrated graphically 800. The figure includes a cardiac cycle graph 802 with associated cardiac cycle designators P, Q, R, S and T. Shown immediately under the cardiac cycle graph 802 is an example of a trigger signal 804 including intervals, $t_o$ having a duration $t_d$. Immediately below the trigger signal 804 is shown an example of an excitation signal 806. The trigger signal and the excitation signal are adapted to occur in a relatively quick part or portion of the cardiac cycle. By a judicious selection of the trigger signal and the excitation signal one can minimize the interference from naturally generated magnetic fields and can simultaneously maximize the detection of the small magnetic perturbations due to the magnetically active agents accumulated in the tissue. The trigger signal and excitation signal can be controlled by a lock-in amplifier and lock-in detection systems can be used to further improve the detection of the small magnetic perturbations due to the magnetically active agents accumulated in the tissue.

The second embodiment of this type of method of the present invention for measuring weak magnetic field perturbations due to locally accumulated magnetically active agents such as nanoparticles at a target location, includes the steps of:

i. placing magnetometer in the proximity of the body;
ii. inserting acoustic radiation force at a target location by an ultrasonic transducer using dual beam ultrasonic transmitter to generate a mechanical vibration of the magnetically active agents in the area of interest at the beat frequency created by the interference of the dual beam ultrasound;
iii. detecting biomagnetic signal by magnetometer such as a SQUID;
iv. applying a modulation to the area of interest to allow phase sensitive detection,
v. localizing loci within the area of interest using an ultrasound probe for data registration, and
vi. transforming the data from step (v) into a data form which indicates presence of nanoparticles at the target location.

Figure 9:
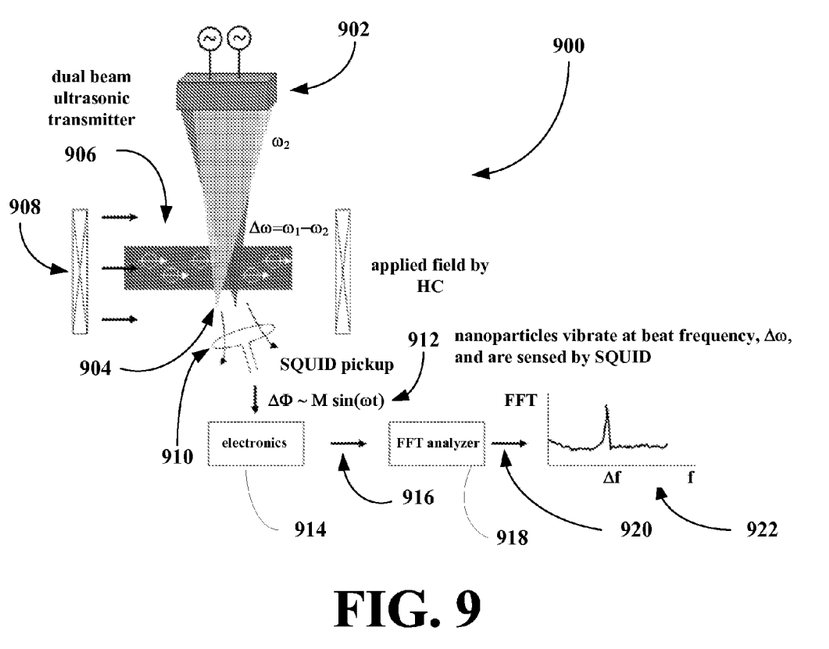
FIG. 9 is a block diagram of a another embodiment of a method embodiment of the present invention.

Referring now to FIG. 9, the above method and apparatus are illustrated graphically 900. The figure includes a dual bean ultrasonic transmitter 902 directed into a location 904 in an area of interest 906 of an animal, including an human containing an amount of magnetically active agents such as magnetically active nanoparticles. The dual beam transmitters 902 produces a mechanical vibration in the location having a frequence $\Delta\omega$ equal to the difference between the two base frequencies $\omega_1$ and $\omega_2$, i.e., Simultaneously, the location is be modulated by application of a controlled external magnetic field from coils 908. A magnetic sensor 910, in this case a SQUID, is positioned adjacent the location 904 and designed to measure a magnetic field distribution of the location 904. A signal 912 from the sensor 910 is forwarded to an electronics unit 914 to produce a data signal 916 which is subjected to a fast Fourier transform analysis in a FFT analyzer 918 to form a data output 920 that can then be graphically outputted 922 to display device or a printing device. The method and apparatus takes advantages of lock-in amplifiers and lock-in detections data processing to improve signal to noise and to improve the detection of weak magnetic signals associated with the magnetically active agents accumulating at different rates and to different concentration in location within an area of interest in an animals body.

The methods and instruments of this invention allow for the detection of areas of injury and infarction of myocardium, liver lesions and tumors, atherosclerotic plaque and other target locations in a body. The methods of this invention can also include the step of positioning the sensor at a first location and moving the sensor along a path to a second position and acquiring a series of magnetic field distributions along the path. The acquisition can be continuous or intermittent, occurring only at discrete intervals along the path. This type of method is ideally suited for coronary arteries and acquiring magnetic field distribution of the heart muscle and arterial walls.

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

We claim:

1. A method for identifying loci in an animal including a human that accumulate magnetically active agents comprising the steps of:
   inserting an intraluminal magneto sensor system including a catheter and a magneto sensor attached to a distal end of the catheter and positioning the sensor adjacent an area of interest (AOI) of the animal,
   administering the magnetically active agents to the animal,
   measuring a first magnetic field distribution of the magnetically active agents in the AOI of an animal with the magneto sensor, and
   determining an amount of the magnetically active agents in the AOI of the animal from the distribution to determine loci within the AOI having high accumulations of the magnetically active agents relative to other locations in the AOI, where the loci may be associated with ischemia, infarction, injury, inflammation, infection, tumor, bleeding, angiogenesis, abnormally high blood barrier permeability, abnormally high capillary permeability, clot formation, plaque, or vulnerable plaque.

2. The method of claim 1, further comprising the step of:
   measuring a second magnetic field distribution in the AOI with the magneto sensor, prior to the administering step,
   comparing the first and second magnetic field distributions, and
   determining loci within the AOI that have an amount of the magnetically active agents above a threshold value.

3. The method claim 1, wherein the sensor is moveable and the method further comprising the steps of:
   moving the magneto sensor to a different AOI of the animal;
   repeating steps of administering, measuring, determining, and the moving steps, and
   determining loci within AOI distributed along an artery or vein that have an amount of the magnetically active agents above a threshold value.

4. A method for measuring weak magnetic field perturbations due to locally accumulation of a magnetically active agent at loci in an animal including a human comprising the steps of:
   i. inserting an intraluminal magneto sensor system including a catheter and a magneto sensor attached to a distal end of the catheter and positioning the sensor adjacent an area of interest (AOI) of the animal into which magnetically active agents were administered,
   ii. monitoring cardiac activity electrically or magnetically of the animal;
   iii. determining a beginning of a trigger signal interval, $t_o$ by analyzing a cardiac cycle waveform of the animal;
   iv. determining a duration, $t_d$ of the trigger signal interval;
   v. generating a trigger signal waveform using parameters determined in steps (iii) and (iv);
   vi. transmitting the trigger signal waveform to an arbitrary-form signal generator in order to generate an excitation signal waveform of chosen duration at the end of trigger;
   vii. transmitting the excitation signal waveform through an excitation coil setup in order to achieve a required polarization of magnetic moments of the magnetically agent;
   viii. repeating steps (ii) through (vii);
   ix. detecting a biomagnetic signal at the magnetometer;
   x. extracting data from the selected interval of the cardiac cycle that equals a length of the excitation signal waveform; and
   xi. transforming the data from step (x) into a data form which indicates presence of the agent at the target location.

5. A method for measuring weak magnetic field perturbations due to locally accumulation of a magnetically active agent at loci in an animal including a human comprising the steps of:
   i. inserting an intraluminal magneto sensor system including a catheter and a magneto sensor attached to a distal end of the catheter and positioning the sensor adjacent an area of interest (AOI) of the animal into which magnetically active agents were administered,
   ii. exciting the AOI with acoustic radiation energy with a dual beam ultrasonic transmitter probe adapted to generate a mechanical vibration of the agents in the AOI at a beat frequency created by an interference of the dual beam ultrasound;
   iii. detecting a biomagnetic signal with the magnetometer,
   iv. applying a modulation to the AOI to allow phase sensitive detection,
   v. localizing loci within the AOI using the probe for data registration, and
   vi. transforming the data from step (v) into a data form which indicates a presence of the agent in the loci of the AOI.

6. An intraluminal magneto sensor system comprising:
   a catheter;
   a thermally insulating housing disposed at a distal end of the catheter, where the housing includes:
     a magneto sensor, and
     optionally other sensors or components,
   a cryogenic fluid circulation assembly including:
     a cryogenic fluid inlet conduit attached to the magnetic sensor and optional other
     sensors or components for supplying a cryogenic fluid to cool the magnetic sensor
     and optional other sensors or components,
     a cryogenic fluid outlet conduit for removing the cryogenic fluid, and
     a source of cryogenic fluid attached to a inlet conduit,
   where the cryogenic fluid circulation assembly cools the magnetic sensor and optional other sensors or components and the thermally insulating housing protects the animal including a human from cryogenic temperatures and where magnetic sensor is adapted to measure loci within an area of interest (AOI) having high accumulations of the magnetically active agents relative to other locations in the AOI and where the loci may be associated with ischemia, infarction, injury, inflammation, infection, tumor, bleeding, angiogenesis, abnormally high blood barrier permeability, abnormally high capillary permeability, clot formation, plaque, or vulnerable plaque.

7. The system of claim 6, wherein the cryogenic fluid is a gas and wherein the magnetic sensor is a SQUID sensor.

* * * * *